United States Patent [19]

Müller

[11] Patent Number: 5,466,466
[45] Date of Patent: Nov. 14, 1995

[54] THERAPEUTIC SYSTEM FOR THE RETARDED AND CONTROLLED TRANSDERMAL OR TRANSMUCOUS ADMINISTRATION OF ACTIVE SUBSTRATES II

[75] Inventor: Walter Müller, Neuwied, Germany

[73] Assignee: LTS Lohmann Therapie-Systeme GmbH & Co. KG, Neuwied, Germany

[21] Appl. No.: 230,448

[22] Filed: Apr. 20, 1994

Related U.S. Application Data

[63] Continuation of Ser. No. 961,215, Oct. 15, 1992, abandoned, which is a continuation of Ser. No. 785,897, Oct. 31, 1991, abandoned, which is a continuation of Ser. No. 478,322, Feb. 12, 1990, abandoned.

[30] Foreign Application Priority Data

Feb. 18, 1989 [DE] Germany .......................... 39 05 050.5

[51] Int. Cl.$^6$ .............................. A61F 13/02; A61K 9/70; A61L 15/16
[52] U.S. Cl. .................... 424/449; 424/448; 424/486; 424/487; 424/488; 514/772.3; 514/772.4; 514/772.6; 514/773
[58] Field of Search .................... 424/448, 449, 424/483, 486, 487, 488; 514/772.3, 772.4, 772.6, 773, 953, 964, 965

[56] References Cited

U.S. PATENT DOCUMENTS 4,781,924  4/1988  Lee et al. .................. 424/449

FOREIGN PATENT DOCUMENTS 0197504  4/1986  European Pat. Off. ..
0249475  12/1987  European Pat. Off. ..

OTHER PUBLICATIONS

C. D. Ebert, "Development of a Novel Transdermal System Design," in 6067 Journal of Controlled Release, 1987, pp. 107–111.

Primary Examiner—Thurman K. Page
Assistant Examiner—Carlos Azpuru
Attorney, Agent, or Firm—Sprung Horn Kramer & Woods

[57] ABSTRACT

The present invention relates to a therapeutic system for the retarded and controlled transdermal or transmucous administration of active substances via an impermeable backing layer, an auxiliary agents containing reservoir, an active substance containing reservoir, and a removable protective layer, characterized in that a. the active substance reservoir comprises the active substance in a non-bioavailable form,
b. the auxiliary agent of the auxiliary agent reservoir renders the active substance bioavailable and
c. auxiliary agent reservoir and active substance reservoir are brought into contact just immediately prior to application or at any time after application, this being done in such a way that the auxiliary agent reaches the active substance reservoir.

16 Claims, 1 Drawing Sheet

THERAPEUTIC SYSTEM FOR THE RETARDED AND CONTROLLED TRANSDERMAL OR TRANSMUCOUS ADMINISTRATION OF ACTIVE SUBSTRATES II

This application is a continuation of application Ser. No. 07/961,215, filed Oct. 15, 1992, now abandoned, which is a continuation of application Ser. No. 785,897, filed Oct. 31, 1991, now abandoned, which is a continuation of Ser. No. 478,322, filed Feb. 12, 1990, now abandoned.

The present, relates to a therapeutic system for the retarded and controlled transdermal or transmucous administration of active substances.

Therapeutic systems are drug-containing devices or forms of administration, respectively, which continuously release one or more pharmaceuticals at a predetermined rate over a fixed period of time to a fixed place of application (see Heilmann, "Therapeutische Systeme", Enke publishers, Stuttgart, 1984, page 24). A transdermal therapeutic system releases the active substance via the skin and thus is applied to the skin, i.e., topically.

The object when using active substances should always be to administer the active substance in an amount which, on the one hand, is as low as possible, and, on the other hand, promises the desired therapeutic effect at maximum certainty. For this purpose numerous, so-called therapeutic systems have been developed which release the active substance in a controlled manner pre-determined by the system parameters. For many systemically effective active substances there is no need or desire to achieve evenly high plasma levels over the whole day.

For example, for some active substances it is of advantage, if the active substance levels are as low as possible during bedtime, and are increased to therapeutically necessary levels only at the end of the sleeping period.

This especially applies to nitro compounds for angina pectoris prophylaxis, since firstly angina pectoris attacks are rare during the night, but occur comparatively frequently in the early morning hours, and secondly the possible development of tolerance in connection with these nitro compounds may be avoided already by an interruption of medication for several hours. A dosage thus adapted to the needs would be desirable as well for nicotine, appetite-suppressing agents, blood pressure influencing agents (β-blockers, α-sympathomimetics), or antiasthmatics (β-sympathomimetics).

A dosage form providing this has to delay the active substance release to the organism for about 4–10 hours after administration in the evening so that therapeutically necessary plasma levels near the end of the sleeping period would arise without further activity of the patient.

The transdermal or transmucous administration of active substances is particularly suitable for such a relatively long retardation time. A transdermal system based on osmotic principles was described in U.S. Pat. No. 4,655,766, EP-A 0249475 described a system based on diffusional processes, and EP-A 0249343 described a system which is activated only on supply of liquids, such as e.g., cutaneous liquids.

Systems according to EP-A 0249475 in principle consist of two separate members, the actual active substance reservoir and an areal agent-free member. The drug-free layer is applied to the complete releasing surface of the reservoir prior to application, and then the system is applied to the skin with the other surface of this drug-free layer. Thus, a concentration gradient with respect to the active substance exists between both members of the system. According to the Fick laws, this results in the fact that the active substance diffuses into this layer being free of active substance and, within a period of time defined by the system parameters, reaches the skin. Thus, the delay period corresponds to the time passed from the moment of combination of the two members of the system, which were separated prior to application, up to the moment at which the active substance is released to the skin in an amount sufficient for the therapeutical purpose.

A disadvantage of this system assembly is the fact that the drug-free retardation layer means an additional diffusion resistance which limits the maximum active substance flux.

Theoretically this disadvantage may be overcome by a system assembly according to EP-A 0249343. In this case, the retardation layer is substituted by a membrane which, after a certain period of time following activation of the system, is switched from "impermeable" to "permeable". The activation may be effected by external or internal supply of a suitable liquid. Said activator liquid may, e.g., be the moisture released by the skin.

One disadvantage of this system is the fact that it is difficult to control the permeability of a membrane with respect to the necessary amount in time by a pre-programmed manner. This particularly applies to that case where cutaneous liquid is used as activator liquid, since individual differences but as well parameters hardly to control, e.g., room temperature or clothings, play an important role.

It was accordingly an object of the present invention to combine the reliability of function of the system assembly according to EP-A 0249475 with the, at least theoretically possible, high active substance flux of the system assembly according to EP-A 0249343.

Surprisingly, this object was achieved by dispensing with a drug-free retardation layer or controllable membrane, respectively, between active substance reservoir and skin, which layer or membrane influences the active substance flux. However, the active substance must not be present in a bioavailable form at the time of application. In the case of transdermal or transmucous application, this means that the active substance can either not leave the system or cannot penetrate into the skin. FIG. 1 shows an embodiment of the system according to the present invention after application and activation.

The active substance in the active substance reservoir is converted into its bioavailable form by the auxiliary agent diffusing from the auxiliary containing reservoir.

In order to avoid that this procedure already takes place during storage, auxiliary diffusion must be excluded until the time of application, at the earliest. This can be done most conveniently in that both systems are supplied separately and are combined to the total system only when applied, e.g., in that at first the active substance reservoir is applied, and then the auxiliary agents containing reservoir is applied with its backing layer on the same site. However, it is possible to use a device as described in EP-A 0249475.

The active substance conversion naturally starts at the bordering surface of the reservoirs and continues in the direction of the releasing surface. That portion of the active substance which is now present in its bioavailable form migrates according to the diffusion laws in the direction of the releasing surface, however, a certain amount migrates into the auxiliary agent reservoir, too. The release rate of bioavailable active substance from the system as a function of time in complicated manner depends on the diffusion coefficient of auxiliary agent in the active substance reservoir, the release rate of auxiliary agent from the auxiliary agent containing reservoir, the diffusion coefficient of the active substance in its bioavailable form in the active substance reservoir, the active substance concentration, the thickness of the active substance reservoir, and the position of the chemical equilibrium for the conversion of the active substance from a non-bioavailable into its bioavailable form.

Despite these complicated dependencies, such a system, once optimized, can be manufactured in an easy and reproducible manner, since its principle of function is based on simple diffusion processes.

In any case, the active substance reaches the intended site, i.e., the skin or mucosa, only after a certain period of time, the desired delaying time.

In order to achieve this retardation time no drug-free layer which limits the active substance flux is required between active substance reservoir and releasing surface of the system.

Systems according to the present invention in principle offer two possibilities of containing the active substance in a non-bioavailable form:

a. the active substance is immobilized
b. the active substance is present as a salt The active Substance is immobilized, if it is bonded to a polymer which itself is not able to diffuse. This is the case, if the active substance is an acid or base and is present as salt of a polymeric polybase or polyacid, respectively.

The production of such salts is a simple acid-base-reaction and necessarily takes place when both components are mixed in a suitable solvent, according to the following equations:

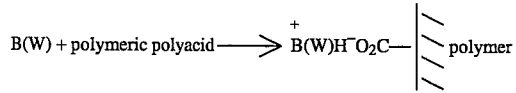

B(W) = active substance base

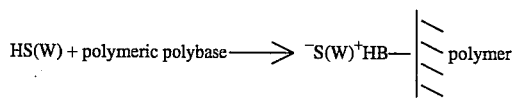

HS(W) = active substance acid

If this reaction is inversed, the auxiliary agent, which, depending on the individual case, is of acidic or basic character, releases the active substance base or active substance acid.

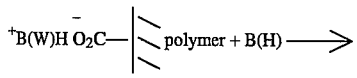

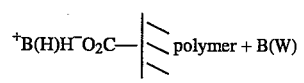

B(H) = auxiliary agent base

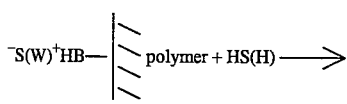

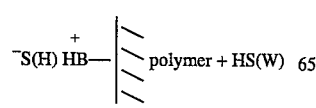

HS(H) = auxiliary agent acid.

Suitable polymeric polyacids or polybases, respectively, are ion exchangers on the basis of artificial resin in their acid or basic form, however, acrylic resins having acidic or basic functional groups are suitable, too. The basic Eudragit E 100 and the acidic Eudragit L 100 or S 100 of Messrs. Röhm-Pharma are particularly suitable among the acrylic resins.

But even if the active substance is present in a form capable of diffusion, it can be rendered non-bioavailable by suitable measures.

Particularly in case of transdermal application of active substances, the lipophilic barrier of the stratum corneum is to be passed. This naturally is particularly difficult for substances of polar or ionic nature. Since most active substances are either bases or acids themselves, it is easily possible to render them so hydrophilic by salt formation that they are able to diffuse within the system as then ionic compounds, but that they may no longer pass the stratum corneum and thus no longer are bioavailable.

In this case, too, the auxiliary agent releases active substance acid or active substance base, respectively, according to the above stated equations. Said base or acid now is present as unloaded molecules so that they are clearly less hydrophilic, and thus can pass the stratum corneum more easily.

In principle, all physiologically acceptable acids, in particular the low monovalent aliphatic carboxylic acids and their derivatives, are suitable as auxiliary agent acids. Examples for suitable acids are: acetic acid, propionic acid, succinic acid, benzoic acid. All physiologically acceptable bases, in particular basic nitrogen compounds, such as, e.g., amines, ethanol amines, glycerine derivatives or other basic derivatives of aminoacid, are suitable auxiliary agent bases.

A further possibility to achieve a delayed active substance absorption is to make use of the bad skin approval of some active substances or active substance derivatives, respectively, and of the possibility to influence them by so-called penetration accelerators. In this case, the active substance is taken up without penetration accelerator, which now is present in the auxiliary agent reservoir as auxiliary agent, at a dosage which is far below the required amount or at an amount below the effective one. Only when the penetration accelerator has passed the active substance reservoir and penetrated the skin, it increases the active substance absorption to the therapeutical required level. Thus, in this case, the active substance reservoir serves as some kind of retardation layer for the penetration accelerator.

A number of substances or groups of substances have been described in literature, which increase the active substance absorption drastically—in some cases this amounts to up to twice the quantity. As example Azone of Messrs. Nelson Research & Development Company, EP-A 0095169 is mentioned.

All materials may be used as materials for the reservoirs or backing layers, respectively, and for the removable protective layer which are commonly used for the production of transdermal and transmucous systems and which are sufficiently known to the man skilled in the art.

Suitable materials for the backing layer, e.g., are foils of polyester, PVC, polyamide, polyethylene, or polypropylene. Commonly used as well are composite foils of these materials, whereby an additional aluminum layer frequently provides for the impermeability to active substances.

In principle the same materials as used for the backing layer are suitable materials for the protective layer, however, in addition they have to be rendered dehesive.

As basic materials for the reservoirs the following materials are mentioned as examples: polyisobutylene, styrene-isoprene-styrene blockcopolymers, polysiloxanes, polymethacrylates, polyurethanes, polyesters, polyamides, and copolymers of ethylene with, e.g., vinylacetate or acrylic acid derivatives.

The reservoirs themselves may be built up as complicated as desired. In particular, additional membranes controlling the release of auxiliary agent to the active substance reservoir and/or the release of active substance in its bioavailable form from the system may be suitable, in order to achieve the desired release profile.

According to a preferred embodiment, the assembly includes a drug-free layer which comprises an acidified buffer.

Figure 1:
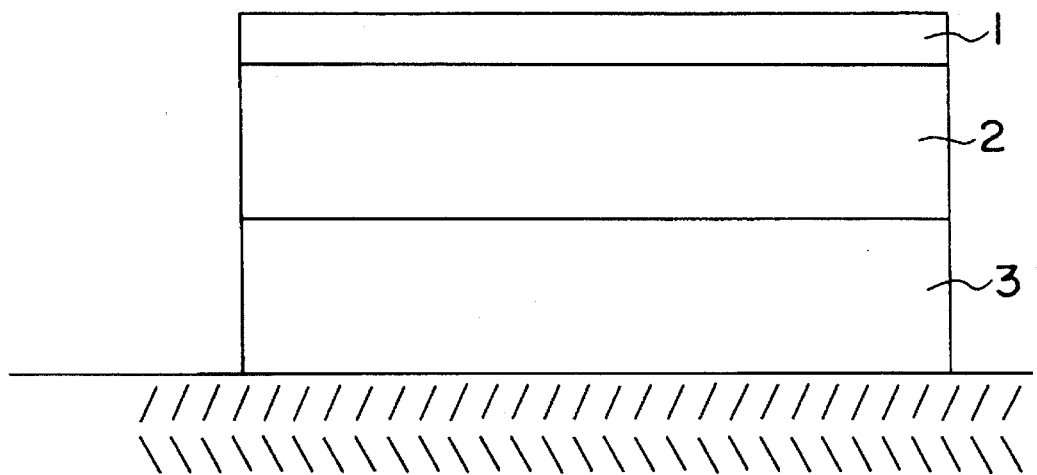
FIG. 1 illustrates the invention, in which 1) represents the backing layer
2) represents the auxiliary agent containing reservoir and
3) represents the active substance containing reservoir.

Suitable active substances, e.g., are nicotine, appetite-suppressing agents, such as norpseudoephedrine, amfepramone, mefenorex, propylhexedrine, fenfluramine, or mazindol, beta-blockers, such as, alprenolol, oxprenolol, penbutolol, bupranolol, metoprolol, betaxolol, atenolol, acebutolol, metipranolol, propranolol, nadolol, pindolol, mepindolol, carteolol, carazolol, timolol, or sotalol, active substances selected from the group consisting of α-sympathomimetics, such as, norfenefrine, octapamine, oxedrine, metaraminol, midodrine, or oxilofrine, as well as active substances selected from the group consisting of β-sympathomimetics, such as salbutamol, terbutaline, fenoterol, clenbuterol, reproterol, hexoprenaline, bamethan, or isoxsuprine. According to a preferred embodiment, the bioactive agent reservoir contacts the site of application either directly via a releasing surface or via a self-adhesive coat. According to a further preferred embodiment, the auxiliary substance reservoir and a bioactive agent reservoir are laminated with one another in order to create the contact allowing the diffusion of the auxiliary substance into the bioactive agent reservoir.

I claim:

1. A method for the retarded and controlled transdermal or transmucous administration of a bioactive agent to the skin, comprising assembling an impermeable backing layer, an auxiliary substance reservoir, a bioactive agent reservoir and a removable protective layer, an acid or basic bioactive agent contained in the bioactive agent reservoir being bonded to a polymer incapable of diffusion, and thus being present in immobilized form as a salt of a polymeric polybase or polyacid, respectively, the auxiliary substance contained in the auxiliary substance reservoir being an acid or a base to convert the bioactive agent salt into a form capable of diffusion when in use the auxiliary substance reservoir and the bioactive agent reservoir are brought into contact, the bioactive agent reservoir and the auxiliary agent reservoir not contacting each other at least until application of the system, removing the protective layer, applying the bioactive agent reservoir to the skin, and contacting the auxiliary substance reservoir with the bioactive agent reservoir.

2. A method according to claim 1, wherein the bioactive agent reservoir contacts the site of application either directly via a releasing surface or via a self-adhesive coat.

3. A method according to claim 1, wherein the auxiliary substance reservoir and the bioactive agent reservoir are laminated with one another in order to create the contact allowing the diffusion of the auxiliary substance into the bioactive agent reservoir.

4. A method according to claim 1, wherein the assembly includes a drug-free layer which comprises an acidified buffer.

5. A method according to claim 1 wherein the auxiliary substance and the bioactive agent are bases and the bioactive agent is bonded to a polymeric polyacid.

6. A method according to claim 1, wherein the bioactive agent and the auxiliary substance are acids and the bioactive substance is bonded to a polymeric polybase.

7. A method according to claim 1, wherein the auxiliary substance is a basic nitrogen compound.

8. A method according to claim 1, wherein the bioactive agent is nicotine.

9. A method according to claim 1, wherein the bioactive agent is an appetite-suppressing agent.

10. A method according to claim 9, wherein the appetite-suppressing agent is norpseudoephedrine, amfepramone, mefenorex, propylhexedrine, fenfluramine or mazindol.

11. A method according to claim 1, wherein the bioactive agent is a beta-blocker.

12. A method according to claim 11, wherein the beta-blocker is alprenolol, oxprenolol, penbutolol, bupranolol, metoprolol, betaxolol, atenolol, acebutolol, metipranolol, propanolol, nadolol, pindolol, mepindolol, carteolol, carazolol, timolol or sotalol.

13. A method according to claim 1, wherein the bioactive agent is an α-sympathomimetic.

14. A method according to claim 13, wherein the bioactive agent is norfenefrine, octapamine, oxedrine, metaraminol, midodrine or oxilofrine.

15. A method according to claim 1, wherein the bioactive agent is a β-sympathomimetic.

16. A method according to claim 15, wherein the bioactive agent is salbutamol, terbutaline, fenoterol, clenbuterol, reproterol, hexoprenaline, bamethan or isoxsuprine.

* * * * *